United States Patent
Wager et al.

(10) Patent No.: US 8,000,978 B2
(45) Date of Patent: Aug. 16, 2011

(54) SYSTEM AND METHOD FOR AUTOMATICALLY GENERATING EVIDENCE-BASED ASSIGNMENT OF CARE PROVIDERS TO PATIENTS

(75) Inventors: Douglas W. Wager, Kansas City, MO (US); Jerald T. Chamberlain, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 1830 days.

(21) Appl. No.: 10/917,337

(22) Filed: Aug. 13, 2004

(65) Prior Publication Data

US 2005/0075904 A1 Apr. 7, 2005

(51) Int. Cl.
*G06Q 10/00* (2006.01)
(52) U.S. Cl. ............................................. 705/2; 705/3
(58) Field of Classification Search .................. 705/2–3; 600/300
See application file for complete search history.

(56) References Cited

U.S. PATENT DOCUMENTS

| | | | |
|---|---|---|---|
| 5,809,477 A | 9/1998 | Pollack | |
| 5,842,173 A | 11/1998 | Strum et al. | |
| 5,995,937 A | 11/1999 | DeBusk et al. | |
| 6,014,629 A | 1/2000 | DeBruin-Ashton | |
| 6,061,657 A | 5/2000 | Whiting-O'Keefe | |
| 6,193,654 B1 | 2/2001 | Richardson et al. | |
| 6,302,844 B1 * | 10/2001 | Walker et al. ................. | 600/300 |
| 6,314,556 B1 | 11/2001 | DeBusk et al. | |
| 7,076,436 B1 | 7/2006 | Ross, Jr. et al. | |
| 7,155,399 B2 | 12/2006 | Andre | |
| 2002/0072911 A1 * | 6/2002 | Kilgore et al. ................. | 704/270 |
| 2003/0050797 A1 | 3/2003 | Brandt et al. | |
| 2003/0050801 A1 | 3/2003 | Ries et al. | |
| 2003/0074222 A1 * | 4/2003 | Rosow et al. ..................... | 705/2 |
| 2003/0101076 A1 | 5/2003 | Zaleski | |
| 2003/0220815 A1 | 11/2003 | Chang et al. | |
| 2004/0039628 A1 | 2/2004 | Thompson et al. | |
| 2004/0267585 A1 | 12/2004 | Anderson et al. | |
| 2005/0182657 A1 | 8/2005 | Abraham-Fuchs et al. | |
| 2006/0047553 A1 | 3/2006 | Fuhrmann et al. | |
| 2006/0047554 A1 | 3/2006 | Larsen et al. | |
| 2006/0053044 A1 | 3/2006 | Kurian et al. | |
| 2006/0074740 A1 | 4/2006 | Garcia et al. | |
| 2006/0143060 A1 | 6/2006 | Conry et al. | |

(Continued)

OTHER PUBLICATIONS

Final Office Action mailed Feb. 19, 2009 for U.S. Appl. No. 10/679,836, 37 pages.

(Continued)

*Primary Examiner* — Gerald J. O'Connor
*Assistant Examiner* — Rajiv J Raj
(74) *Attorney, Agent, or Firm* — Shook, Hardy & Bacon (57) ABSTRACT

Care provider assignments to a patient may be automatically generated based on clinical evidence, documentation, workload, infectious status and other factors. The patient's chart may be accessed by a rules-based engine configured with rules to relate a patient's clinical status and needs to qualifications, certifications, capabilities and skills of care providers to select the care provider best qualified to assign to the patient. For instance, care providers having specialized training may be identified for assignment to patients presenting with specialized needs. Graphical displays of available providers may be displayed to and overridden by a manager. Because patient needs are automatically aligned with provider capabilities, availability and other factors, the errors, oversights and inefficiencies of manual or informal assignment systems are avoided and better health care delivery can be realized.

47 Claims, 4 Drawing Sheets

U.S. PATENT DOCUMENTS

2006/0143061 A1  6/2006  Sharper et al.

OTHER PUBLICATIONS

Final Office Action mailed Jan. 4, 2010 for U.S. Appl. No. 11/025,969, 21 pages.
Non-Final Office Action mailed Jun. 4, 2008 for U.S. Appl. No. 10/679,836, 27 pages.
Non-Final Office Action mailed Apr. 28, 2009 for U.S. Appl. No. 11/025,969, 12 pages.
Non-Final Office Action mailed Aug. 3, 2009 for U.S. Appl. No. 10/679,836, 28 pages.
Final Office Action mailed Dec. 3, 2010 regarding U.S. Appl. No. 11/025,969, 23 pages.
Final Office Action mailed May 4, 2010 for U.S. Appl. No. 10/679,836.
Office Action mailed Jun. 1, 2010 for U.S. Appl. No. 11/025,969, 21 pages.
Non-Final Office Action mailed Jun. 1, 2010 regarding U.S. Appl. No. 11/025,969, 21 pages.
Non-Final Office Action mailed Aug. 31, 2010 regarding U.S. Appl. No. 10/679,836, 37 pages.

* cited by examiner

SHIFT ASSIGNMENT

LOCATION: PICU  SHIFT: TODAY 1900-0700

PROVIDERS

| PROVIDER | LOAD | ASSIGNMENTS | | |
|---|---|---|---|---|
| Heather Brown, RN | 64 | 16a | Wilson, David 8y M | |
| | | 18b | Hudson, Stacey 8y F | |
| | | 18a | Moore, Larry 5y M | |
| Diane Fuller, RN | 76 | 4a | Brown, Rebecca 17y F | |
| Clive Peacock, RN | | | | |
| Linda Smith, RN | | | | |
| William Walker, RN | | | | |

ASSIGNMENTS

PICU 1
- 1a  Empty (Opening)
- 2a  Wallace, Jerry 8y M (Pending)
- 2b  Empty
- ✓ 4a  Brown, Rebecca 17y F
- 4b  Empty
- ✓ 6a  Robertson, Bruce 17y M

OPTIMIZE ASSIGNMENT

PATIENT: 2a Wallace, Jerry 8y M (Pending)  CC: Meningitis

ASSIGNED PROVIDER: Linda Smith, RN  Phone Number: (816) 555-4546  Pager: (816) 555-9054  Load: 78

| ASSIGNMENT OPTIONS | | | |
|---|---|---|---|
| Linda Smith, RN | 74 | Add: | 2a Wallace, Jerry 8y M |
| | | Drop: | 8b Palmer, Glen 3y M |
| Heather Brown, RN | 84 | Add: | 8b Palmer, Glen 3y M |
| Linda Smith, RN | 74 | Add: | 2a Wallace, Jerry 8y M |
| | | Drop: | 8b Palmer, Glen 3y M |
| William Walker, RN | 83 | Add: | 8b Palmer, Glen 3y M |
| | | Drop: | 14b Kerns, Patricia 14y F |
| Diane Fuller, RN | 74 | Add: | 14b Kerns, Patricia 14y F |

(NEW SHIFT) (SAVE SHIFT) (CLEAR ALL ASSIGNMENTS) (MAKE ASSIGNMENT) (OPTIMIZE ASSIGNMENT)

SYSTEM AND METHOD FOR AUTOMATICALLY GENERATING EVIDENCE-BASED ASSIGNMENT OF CARE PROVIDERS TO PATIENTS

CROSS-REFERENCE TO RELATED APPLICATION

The subject matter of this application is related to the subject matter of copending U.S. patent application Ser. No. 10/679,836 filed Oct. 6, 2003, entitled "Computerized System and Method for Determining Work in a Healthcare Environment", assigned or under obligation of assignment to the same entity as this application, which application is incorporated by reference herein, from which application priority is claimed, and of which this application is a continuation-in-part.

STATEMENT REGARDING FEDERALLY SPONSORED RESEARCH OR DEVELOPMENT

Not applicable.

FIELD OF THE INVENTION

The invention relates to the field of clinical workforce management, and more particularly to tools and techniques for automatically filtering and assigning care providers to hospital and other patients based on a matching of the clinical requirements of those patients to provider factors including clinical qualifications or certifications, the exposure of the provider to other infectious patients, the estimated workload represented by those patients and the provider's capacity to perform that work, among other clinical evidence and factors.

BACKGROUND OF THE INVENTION

The task of supervising the assignment of health care providers to hospital and other patients has often fallen to managers such as charge nurses or others without the aid of systematic tools or guides. In many hospitals and other facilities a nurse manager, charge nurse or other personnel with staffing responsibility may often manually fill out a schedule sheet to assign individual patients from patient lists to nurses, technicians and other clinical care personnel for a given shift, day or other period. That clinical manager may resort to informal rules, intuition and estimates concerning which care provider may be qualified, appropriate or available to service a particular patient. The clinical manager may informally take into account the patient's documented clinical condition such as acuity, age, the estimated workload represented by that patient and other indicators as well as the provider's own qualifications, training and clinical considerations including potential exposure to other infectious patients.

The task of appropriately tailoring care provider assignments to the needs of individual patients can become even more challenging since provider schedules may change significantly from day to day, for instance as nurses, technicians and others call out sick, change or overstay their shifts or take leave days. Patient assignments may likewise rapidly change as the patient population changes over the course of a shift, day other schedule period, or when the acuity or other status of patients themselves change. Because of these scheduling pressures and the improvised nature of assignments in many cases, the quality and appropriateness of the clinical match between a patient's provider team and the medical needs of that patient may be inconsistent or less than optimal over time. In general such manually generated assignments may not be systematically optimized or validated against clinical best practices or otherwise. In worst cases, a provider who is not qualified or competent to support a patient's clinical needs, for example a nurse not certified to operate a ventilator or pump, may be assigned to a patient requiring that type of attention. In other scenarios a care provider with recent potential exposure to infectious agents may be assigned to immune-compromised or other patients to whom they may act as a disease carrier. Likewise a patient representing a high workload commitment may be assigned to a provider whose capacity is already fully extended. Other problems in clinical workforce management exist.

SUMMARY OF THE INVENTION

The invention overcoming these and other problems in the art relates in one regard to a system and method for automatically generating evidence-based assignments of care providers to patients, in which a rules-based assignment engine may perform a thorough, programmatic comparison between patient needs and requirements and care provider factors including qualifications, skills, patient workload, infectious exposure, provider availability and other factors. In embodiments, the assignment engine may access a patient's medical chart or other clinical documentation or records to identify necessary qualifications or factors which may guide the assignment of nurses, doctors, technicians and other care providers to that patient. The platform and techniques of the invention may in one regard generate an assignment of each patient in a unit or department to the care provider having a best, closest or sufficient match to the clinical needs of that patient, consistent with workload, infectious or other constraints. In cases, clinical or epidemiological factors such as potential exposure or assignment to other patients having identified classes of infectious disease may be used to rule out the assignment of given providers to individual patients. According to embodiments of the invention in a further regard, a clinical manager may manipulate a management application or interface to accept or override given provider assignments, to evaluate alternate providers for assignment to individual patients under different conditions, to view resulting matches to patient requirements, to adjust various schedules and view other simulations or projected results or schedules. According to embodiments of the invention in a further regard, the management interface may flag potential conflicts between a provider's background and a patient's clinical needs. For example a supervisor may be alerted that the reassignment of a care provider to a patient may be contraindicated by skill, certification, infectious status, scheduling or other factors.

DETAILED DESCRIPTION OF EMBODIMENTS

Figure 1:
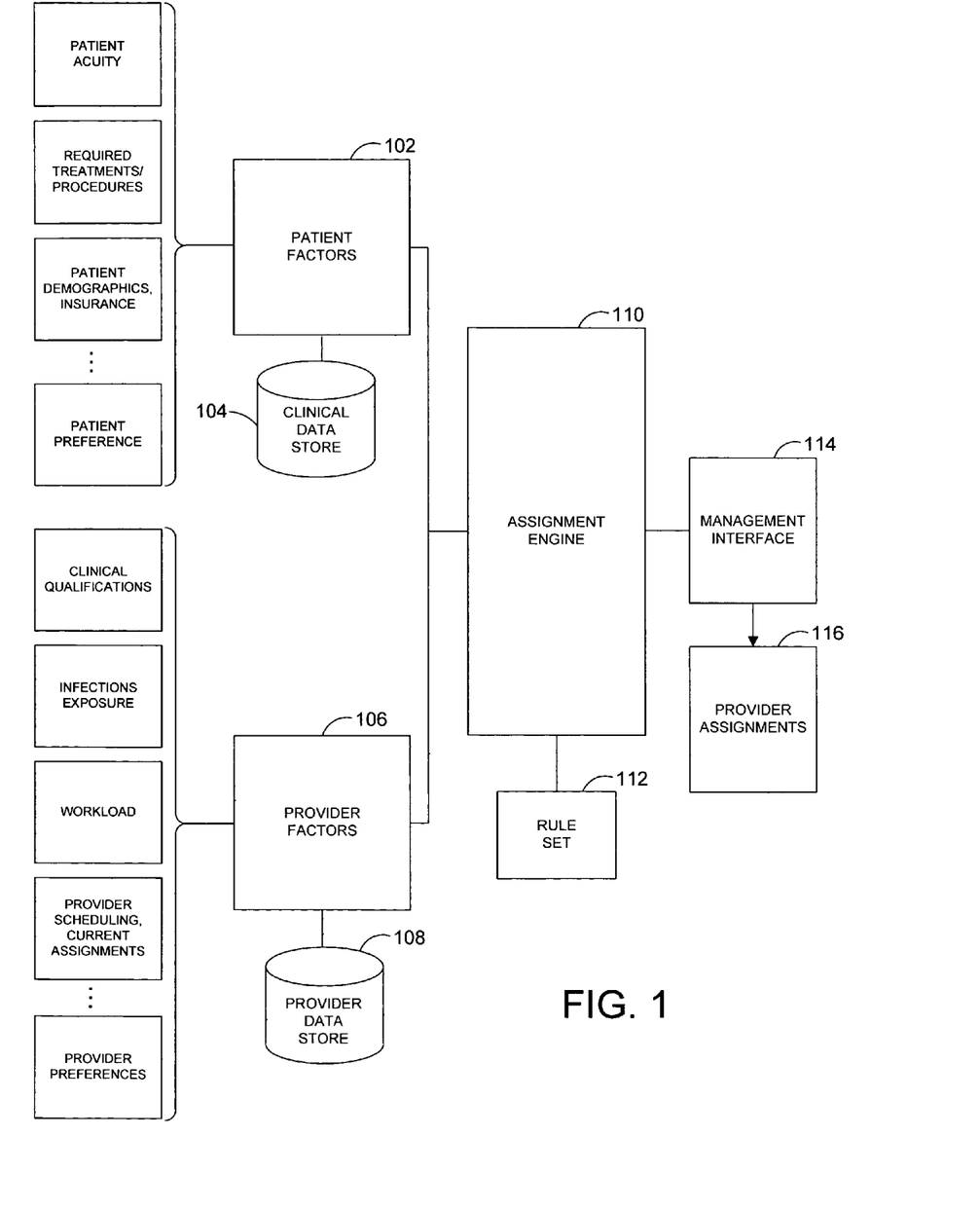
FIG. 1 illustrates an environment in which a platform for automatically generating evidence-based assignments of care providers to patients may operate, according to embodiments of the invention.

FIG. 1 illustrates an environment in which a system and method for automatically generating an evidence-based assignment of care providers to one or more clinical patients may operate, according to embodiments of the invention. As illustrated in that figure, in embodiments an assignment engine 110 may communicate with a set of networked clinical resources including a clinical data store 104 and a care provider data store 108 to analyze and automatically generate clinical staffing assignments appropriate to patient needs. According to embodiments of the invention in one regard, a supervisor or manager such as a nurse manager, charge nurse, a physician or other person with staff assignment responsibilities may operate a management interface 114 or other application, such as a graphical user interface on a computer workstation, to view care provider assignments, patient census and other operational data. According to embodiments of the invention, the clinical environment and networked clinical tools may in one regard be, include or interface to environments and resources described in the aforementioned copending U.S. patent application Ser. No. 10/679,836, or others.

Clinical sites or environments in which the assignment platform of the invention may operate may include for example a hospital, a research facility, an out-patient facility, a government or university facility, or other medical or clinical facility or site. In embodiments, the supervisor tasked with assigning care providers to patients may access the management interface 114 to generate and view the staff assignments for a shift, a day or longer periods such as a week, two week or month schedule, or other intervals or times. In further embodiments, the assignments may be generated on a case or procedure basis rather than a shift basis, for instance to assign qualified personnel to a scheduled surgical or other procedure.

According to embodiments in one regard, the care provider staff managed and assigned to the patient population according to the invention may include care providers such as nurses such as registered or licensed practical nurses, technicians such as X-ray, MRI (magnetic resonance imaging) or other imaging technicians, phlebotomists, medical assistants, paramedics, therapists, physicians, surgeons, psychiatrists, dentists, hygienists, or other clinical practitioners or staff. In cases it may be the responsibility of the supervisor to review and assign care providers to the patient population every day before or during each shift. In other cases the manager may review and generate or update assignments on an ad hoc basis or at irregular times, for example when the patient census may change, when the acuity or other status of existing patients changes, or at other times.

When the supervisor or other user operates the management interface 114 or other application for purposes of managing care provider assignments, that interface or other application may communicate with the assignment engine 110 to initiate the process of generating an assignment of care providers to patients for the shift, day or other period. In embodiments the assignment engine 110 may be or include a rules-based assignment engine, which may include or interface to a set of resources including a rule set 112 (illustrated e.g. in FIG. 2). Rule set 112 in general may encode a set of relationships which associate patient needs and requirements with care defined provider factors including clinical competencies, workload criteria, scheduling, infectious exposure status or other clinically related or other information. In embodiments, each of assignment engine 110 and rule set 112 may be or include a self-learning network such as a neural network, support vector machine or other machine or resource.

To correlate patient needs with provider resources, the assignment engine 110 may access a set of patient factors 102 as well as a set of corresponding provider factors 106 to match available and qualified care providers with the documented clinical needs of the current patient population, in light of rule set 112 or other assignment or qualification logic. The patient factors 102 may include, for example, clinical notations and information from a patient chart, an electronic medical record, a patient history, test or laboratory results, X-ray, MRI or other images, a record of prescribed pharmaceuticals, patient morbidity status, patient mobility status, or other medical, clinical or other data. For instance, a requirement for one-to-one provider assignment may also be included in patient factors 102. Patient factors 102 may further include an estimated workload represented by the patient, for instance as described in the aforementioned copending U.S. patent application Ser. No. 10/679,836, or otherwise. Patient factors 102 may likewise include demographic information such as for instance patient age, gender, ethnicity, marital status, or additional information such as insurance information, residence address, treatment location, scheduled procedures or procedures, or other clinically relevant or other data. For example, a patient's do not resuscitate (DNR) or living will status, personal preferences such as language, religious or dietary preferences, or other personal or clinical factors or inputs may also be included in patient factors 102. Patient factors 102 may for example be acquired via emergency room or other intake forms, from physician interviews, medical smart cards, databases or other sources.

The provider factors 106 may on the other hand include data such as provider education, clinical certifications such as board, state or other certifications for specified procedures or treatments, or indications of experience, skills or competency to perform or operate the same. Those procedures, treatments, skills and related activities may for example include a specific model or brand of ventilator or pump or other technology operation, intravenous blood draws, intubations, cardiac care such as advanced cardiac life support (ACLS) and intra-aortic balloon pump (IABP), cardiac or other catheterizations, surgical or anesthesiology qualifications, qualification or experience in cardio-pulmonary or "crash-cart" resuscitation, life support, pediatric care such as pediatric advanced life support (PALS), neonatal care such as neonatal resuscitation provider (NRP), qualification to store, dispense or administer prescription pharmaceuticals or other drugs, or other competencies, experiences, skills or corresponding limitations.

According to embodiments in a further regard, provider factors 106 may likewise include acuity or workload ratings for a care provider indicating their availability or capacity to undertake new patient assignments, given for instance the number and nature of existing patient assignments, work schedules or other workload factors. Workload ratings or estimates in provider factors 106 may for example be computed or generated according to the techniques described in the aforementioned copending U.S. patent application Ser. No. 10/679,836, or others. Provider factors 106 may likewise in cases include rating, evaluation, seniority or other data for providers within their organization or clinical unit.

Provider factors 106 may furthermore incorporate short or long-term provider schedules, which may for example be accessed or input via separate scheduling applications, manual calendars or other scheduling or other information or sources. Provider factors 106 may also include a history of the provider's past or ongoing patient assignments, unit or floor assignments and other schedule and assignment details. In embodiments, the providers may be given access to provider factors 106 to directly input various factors, including preferences, themselves, for instance via a computer workstation or other interface. The provider factors 106, like the set of patient factors 102, may be likewise accessed, updated or selected by supervisory staff or others to identify, adjust or reorder those parameters which are meaningful to patient care, including to clinical outcomes.

In general, in the context of workforce management there is an objective to avoid mismatches in provider assignments such as assigning inexperienced or untrained personnel to the sickest or most acute patients (a skillset mismatch), assigning all or too many of the sickest or most acute patients to just one experienced provider (a workload imbalance), or assigning the same provider to both a potentially infectious or contagious patient and an immune-suppressed patient (an infectious or patient/patient mismatch). Embodiments of the invention in one regard address these scenarios and others by providing a mechanism for systematic provider assignments which incorporate clinically relevant and other criteria to avoid those conflicts as part of the logic of those assignments, at the outset.

Towards those purposes, when a set of patient factors 102 and provider factors 106 have been accessed, the assignment engine 110 may generate a comparative analysis between the set of patient needs reflected in patient factors 102 and the provider factors 106 of the provider staff available to deliver the needed care. The assignment engine 110 may apply the rule set 112 to the set of patient factors 102, provider factors 106 and other data to conduct that comparison and generate an appropriate set of provider assignments 116 as a result. The set of provider assignments 116 may thus reflect optimized, best-fit, sufficient or appropriate assignments of available nurses, physicians, technicians, therapists and other provider staff to the clinically documented needs of the patient population.

Figure 2:
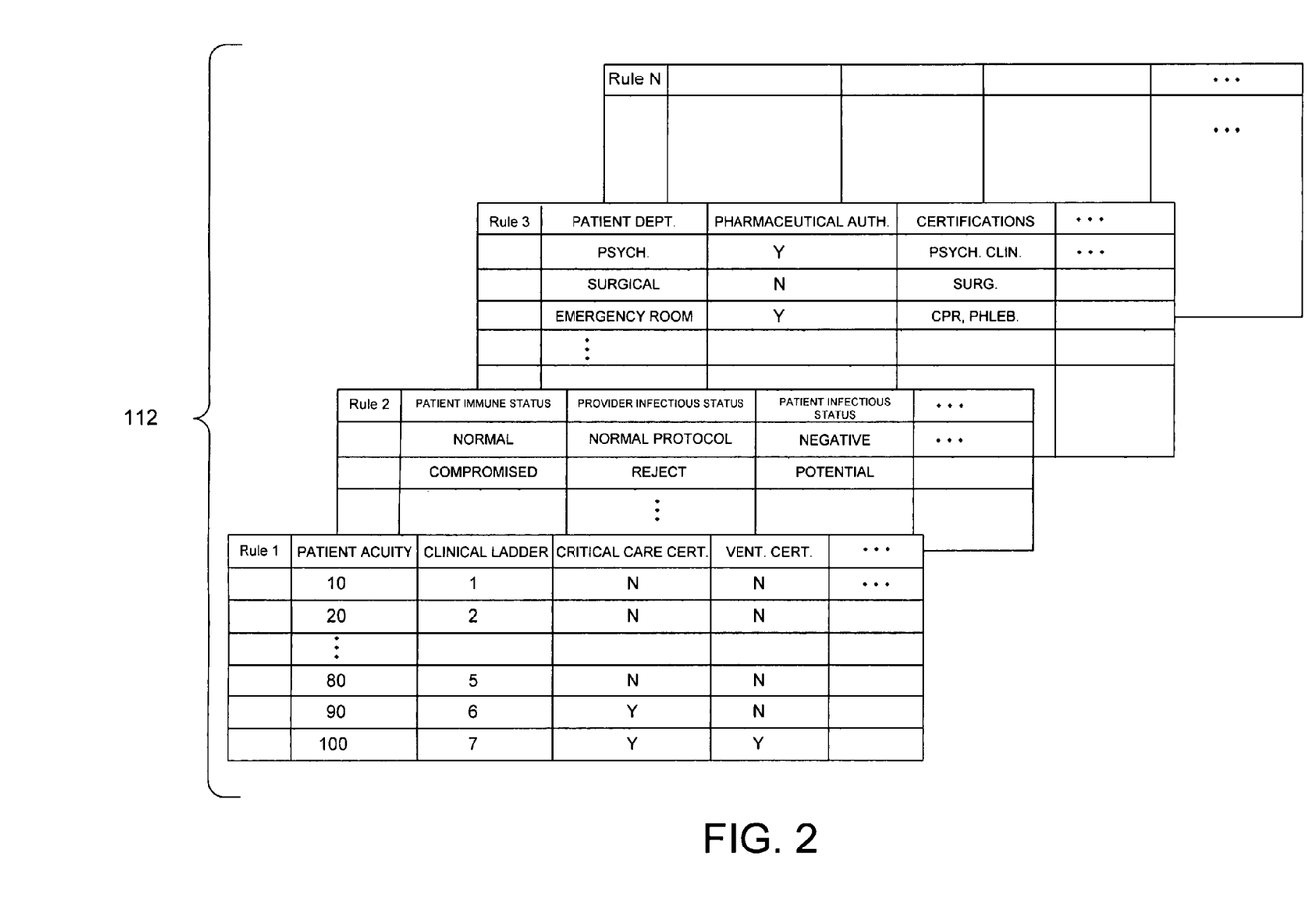
FIG. 2 illustrates an exemplary rule set for generating assignments of providers to patients, according to embodiments of the invention.

As more particularly illustrated in FIG. 2, the rule set 112 guiding the assignment of providers to patient may consist of or include one or more set of logical or conditional relations between the set of patient factors 102 or other documented patient requirements on one side, and the provider factors 106 or other care provider qualifications or factors on the other. As illustrated in that figure, a patient may for instance be assigned an acuity rating (illustratively 0-100 but other scales or ratings may be used), depending on the severity, length or other characteristics of the patient's disease or condition. A high acuity rating of 100 for a patient may indicate a requirement for a nurse, physician, technician or other provider staff who has attained a comparatively high stage on a clinical ladder or other experience scale, while also requiring certifications such as critical care, ventilator or other equipment operation, or other criteria. That requirement may be reflected in a minimum experience rating necessary to support that patient, or otherwise.

Conversely a low acuity rating of 20 may permit a comparatively relaxed set of provider skills or qualifications, so that ventilator certification or other qualifications may not be necessary for assignment to that patient. It may be noted that in embodiments a provider with such comparatively greater skill sets may still be assigned in cases to lower acuity patients, for instance when the patient population is low. The rule set 112 may in one regard be extensible, updateable and managed to ensure or reflect best clinical practices in the relationship between the set of patient factors 102 and the provider factors 106. The rule set 112 may in embodiments be expressed in table form as shown, or in lists, matrices or other formats or configurations. In further embodiments the rule set 112 be accessed on a subscription or other basis from a third party, or generated or maintained internally by a hospital or other organization.

In embodiments, the assignment engine 110 may compare the provider factors 106 for each provider available for a given patient against the criteria in rule set 112 or other matrix or template, and identify all providers qualified to service the clinical needs of that patient. For instance all providers having a clinical ladder rating above 6 may be identified, or all providers certified for urgent procedures ("crash-cart") such as resuscitation, life-support or related procedures may be listed. In embodiments, the assignment engine 110 may generate a weighted rating or sliding scale of matches between various patient factors 102 and provider factors 106, to identify or rank candidate providers for a patient.

According to embodiments of the invention in one regard, the rule set 112 may in implementations assign the greatest or primary weight to matching the patient's clinical acuity with the skills or competencies of the available providers, to ensure a commensurate level of clinical experience, training and judgment to the patient's condition. According to embodiments in another regard, the logic of rule set 112 may assign a next-greatest weight to factors related to continuity of care, that is, to ensure that a doctor, nurse, therapist, technician or other provider who was been assigned to and supported a patient previously may continue to be assigned to that patient, to enhance their familiarity with the patient's history and responses. In a further regard, rule set 112 may assign a further next-greatest weight to the workload of the provider, and the impact that the incremental workload represented by the patient may have on that provider. Again, according to embodiments of the invention the workload discharged by a provider and/or the workload represented by a patient may be computed or estimated according to techniques described in co-pending U.S. patent application Ser. No. 10/679,836, or others.

In a yet further regard, the rule set 112 may assign a further next-greatest weight to expressed provider or patient preferences, such as those which for example are not strictly clinically or work-load based. Those may include for example a preference to work on a certain floor or wing of a unit, to work overtime or holiday shifts, to work with certain other providers, or other non-clinical or other preferences. Other orderings, weightings and preferences are possible. In embodiments, the sequence or ordering of factors evaluated in rule set 112 may be reordered or re-weighted according to or based on clinical discretion, outcomes or for other reasons. In embodiments such reordering may be implemented for instance by clinical policy, for example instance issued by a department head, medical director, staff manager or other source.

According to embodiments of the invention in another regard, the assignment engine 110 and rule set 112 may also apply a set of criteria for infectious exposure to all potential matches between providers and patients. That is, and in embodiments before, after or independently from acuity and other ordered rules, the assignment engine 110 may examine the patient factors 102 and provider factors 106 to determine whether a provider may have or could have had potential exposure to infectious agents, communicable diseases, pathogens or infectious pathways which should eliminate them as providers for immune-compromised or other patients.

For instance, a nurse, technician or other provider who has cared for a patient having a methicillin resistant staphylococcus aureus (MRSA) or persistent influenza infection may be prohibited from being assigned to a patient having diagnosed HIV disease, or to a patient undergoing chemotherapy. That potential exposure may be tracked in cases over the last two weeks, month or other clinically relevant or other amount of time, for instance via the provider's assignment history. That history may be examined for example to ensure or verify that the provider is outside any initially infectious period indicated by a pathogen or communicable disease, and therefore may not act as a possible carrier for that agent. Other infectious or epidemiological factors may be taken into account. For instance, a provider who has reported a needle-stick from an intravenous blood draw testing for a bacterial meningitis infection may be prohibited from being assigned to any patient for a period of one week or other time, or until for example that provider is tested and receives a confirmation of their own infectious status. Providers assigned to a patient in infectious isolation or quarantine may likewise be prohibited from assignment to other patients, for instance until some period after discharge of that patient. Likewise, the assignment engine 110 may ensure that patients in late-term pregnancy not be assigned providers having any possible infectious exposure in the last three months.

In embodiments, the assignment engine 110 may further examine provider factors 106 to determine whether a provider could have come into potential contact with an infectious agent, even if not directly assigned to or responsible for infectious patients in the past. For example, the provider's assignment history may be examined to determine whether the provider may have come in contact with other providers, for instance on the same shift, who themselves were potentially exposed to pathogens or agents. Thus, patient/provider/patient as well as provider/provider/patient pathways or other extended infection routes may be examined. The history of infectious patients located in the provider's floor unit or other prior assignments may likewise be examined. Other conditions, criteria, history, pathways or indicators related to infectious status may be similarly evaluated.

In embodiments when only one provider meets all threshold criteria encoded in rule set 112, the assignment engine 110 may assign that provider to the patient in question. In embodiments when more than one provider meets all threshold criteria, one appropriate provider may be selected from the pool of qualified providers, for example by a narrowing process conditioned on further factors. Such further factors may include for example schedule preferences, staff seniority, or others. In other embodiments when multiple providers satisfy the criteria of rule set 112, the first available provider from the group of qualified providers may be selected, or random, round-robin or other selection techniques may be applied. When the assignment engine 110 has completed the processing of patient factors 102 against provider factors 106 using rule set 112, the assignment engine 110 may generate a set of provider assignments 116 as an output. The set of provider assignments 116 may indicate which provider or providers may be assigned to which patient or patients, during what shift or other period, and what clinical or other tasks or responsibilities the provider may take on for that patient.

Figure 3:
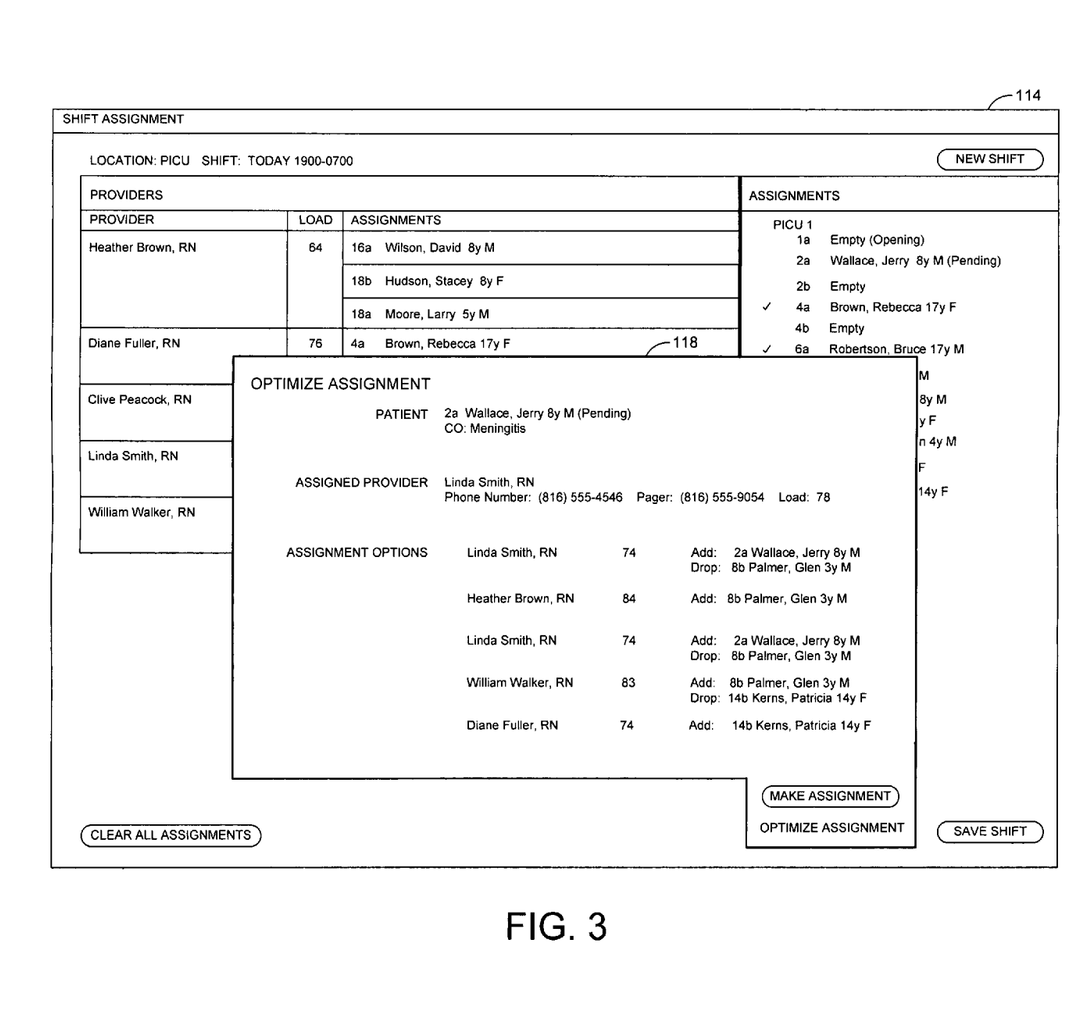
FIG. 3 illustrates a management interface for selecting provider assignments and other variables, according to embodiments of the invention.

According to embodiments of the invention in another regard, and as illustrated for instance in FIG. 3, in operation the supervisor or other user operating the management interface 114 may be presented with a selector tool 118, to view, edit, manipulate or store the set of provider assignments 116 which have been generated via the assignment engine 110. More particularly and as shown, the selector tool 118 may display the set of provider assignments 116 to the supervisor or other user, and present dialogues to permit the user to accept, override, edit or otherwise manipulate the assignments of care providers to one or more patients.

For instance, a nurse manager or charge nurse may conclude that the condition of a given patient is trending in a more acute direction, and therefore may wish to assign a nurse or other staff with a higher clinical ladder rating than initially indicated in the set of provider assignments 116. Or, the supervisor may choose to split the assignment of a given patient between two or more providers during a shift. Other adjustments or updates are possible. The supervisor operating the management interface 114 may in cases choose to accept the generated assignments without alteration. Once the set of provider assignments 116 are generated, updated as desired and accepted, the set of provider assignments may in embodiments be communicated or transmitted to the care providers being assigned. Those assignments may be communicated for example by email, page such as voice page or alphanumeric page, by the distribution of printed copies to those personnel, or through other channels or media.

In embodiments of the invention in another regard, during the selection and updating process the selector tool 118 and/or management interface 114 may display an alert when the assignment of a given provider to a patient may be contraindicated. For example this could occur again when a nurse, physician or other provider who has recently been assigned to an immune-compromised patient could potentially come in contact with an infectious patient, or when a provider's schedule for the next two weeks or other period will not permit patient continuity. The corresponding alert or notice may be presented when the user attempts to assign or reassign a provider to a patient when using selector tool 118 or other times. In embodiments that alert may be accompanied by an indication of the next-best or other provider fit, excluding the contraindicated individual.

In further embodiments, the assignment engine 110 may also predicate assignments in the set of provider assignments 116 on additional or external factors or constraints. For example, the assignment engine 110 may condition the set of provider assignments 116 on maintaining total patient-to-provider ratio such as may be stipulated by state or other regulations, or to limit total working hours for a week or other period within occupational or other guidelines. Other external or other constraints or factors may be applied.

As noted, a charge nurse or other supervisory personnel may operate management interface 114 to generate a set of provider assignments 116 on a scheduled basis, such as a shift, day, week or month, or on an event or case basis, such as a scheduled or unscheduled surgery or other procedure. According to embodiments of the invention in another regard, charge nurse or other floor or clinical managers may also initiate an updated set of provider assignments 116 on an ad hoc basis or at irregular times. Such ad hoc updates may for instance be triggered by changed conditions such as when a patient census changes, the acuity of existing patients changes, the set of available providers changes, for instance when nurses, technicians or others take sick leave, remain after their shift due to urgent procedures or depart before the end of their shift, or either the patient population or provider population changes in some other unpredictable or unscheduled manner. At those or other times, an updated set of provider assignments 116 may be generated during the middle of a shift or other period, to accommodate the changing clinical conditions.

In such instances and at other times, according to embodiments of the invention the assignment engine 110 may begin processing with, and as much as possible attempt to maintain, the previous set of provider assignments 116. Assignment engine 110 may do so, among other objectives, to preserve continuity of patient care, as well as to maintain the schedules and assignments under which the assigned providers have already been operating. In those regards, when an intra-shift or other ad hoc update to the set of provider assignments 116 occurs, in embodiments the assignment engine 110 may only adjust the minimum set of assignments necessary to satisfy the new patient needs or other changed conditions. In those cases, for example, one nurse may be reassigned to a newly arrived trauma patient during a current shift, while a replacement for that nurse for other patients who were under that provider's care may be selected to preserve the greatest possible continuity among remaining patients, and their currently assigned providers. Other protocols for mid-shift or other ad hoc or irregular reassignments are possible. In cases those could include, if desired, a partial or total recompilation of the entire set of assignments 116 with some or all assignments determined anew, for instance if circumstances warrant, supervisors prefer or providers suggest. It may also be noted that according to embodiments of the invention, the assignment engine 110 may likewise generate a set of assignments 116 likewise incorporating the least amount of changes or perturbation to existing assignments when that engine may generate assignments which are not ad hoc or intra-shift, but are instead generated on a regular or scheduled basis, as well.

Figure 4:
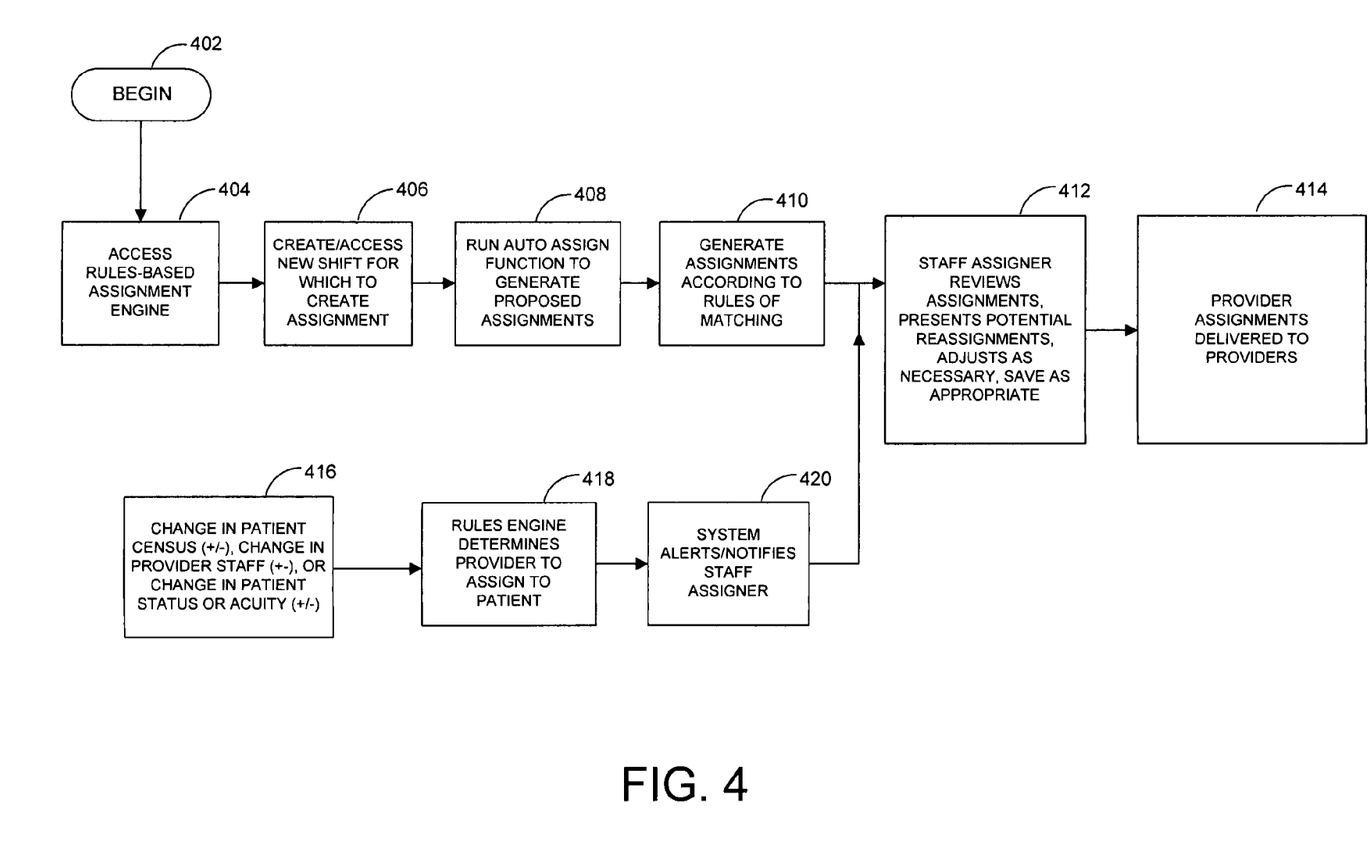
FIG. 4 illustrates a flowchart of overall provider assignment processing, according to embodiments of the invention.

Overall assignment processing according to embodiments of the invention is illustrated in FIG. 4. In step 402, processing may begin. In step 404, the assignment engine 110 may be accessed or activated, for instance using management interface 114. In step 406, a new shift or period, such as an 8, 12, 16 hour shift or other interval for a given date, or other scheduling period such as a week or other interval, may be created or accessed. In further embodiments the assignments may be opened for a case or event rather than a shift or schedule, such as a surgery or other procedure. In step 408, an administrator or other user may execute an automatic assignment or similar function, for instance automatically accessing the clinical data store 104 and provider data store 108 to generate reports or matches between provider factors 106, qualifications, schedules and other data and clinical patient needs reflected in patient factors 102. In step 410, the assignment engine 110 may generate the set of provider assignments 116 reflecting the assignment or pairing of one or more care providers to one or more patients, for instance detailing that a nurse, physician, technician or other clinical personnel will be assigned to or responsible for a given patient for a shift, for certain hours that day or during an identified event.

Before, after or concurrently with steps 404 through 410, processing may also accommodate and accept mid-shift assignments or reassignments due to patient intake, discharge or other changes on a dynamic or unscheduled basis. In step 416, a change in patient census or population, a change in available care provider personnel, such as due to early arrival or departure, a change in patient status or acuity or other clinical or staffing change may be noted and input to the system, for instance via management interface 114 or otherwise. In step 418, an assignment of one or more providers to the new patient or patient with changed status may be generated by assignment engine 110, in the form of a whole or partial update to the set of provider assignments 116 or otherwise. In step 420, the system may alert or notify a clinical manager or other person with staff assignment responsibilities of the assignment, for example via management interface 114, by page, email or other alert or notification.

In step 412, for instance following either step 410 or 420, the clinical manager or other person with assignment responsibilities may review the generated set of provider assignments 116, which may for example be recorded in list, table, matrix or other form, again for instance via the management interface 114. That manager may in cases elect to accept, override or modify the set of provider assignments 116 generated by the system, according to their clinical discretion or judgment. After any modifications or updates, the manager may accept and save the set of provider assignments 116 to the system. In step 414, the care providers whose assignments are being managed under embodiments of the invention may be provided with a notification or copy of their patient or other clinical assignments, for example by printed copy of the assignments, email, page such as voice page or alphanumeric page, though logging in to a Web or other network site, or via other channels. In step 416, processing may repeat, return to a prior processing point, proceed to a further processing point or end.

The foregoing description of the invention is illustrative, and modifications in configuration and implementation will occur to persons skilled in the art. For instance, while the invention has generally been described in terms of one manager operating one management interface 114 to manipulate provider-to-patient assignments, in embodiments multiple screens, workstations or other interfaces could each present a view on provider resources and other variables, for instance permitting multiple managers to manage one or more units at the same time, separately or together. The management interface 114 may likewise itself in embodiments be presented via remote access, such as a remote Internet connection or via a network-enabled wireless device.

Similarly, while the invention has in embodiments generally been described as generating one-to-one provider to patient assignments, in embodiments assignments may be generated which pair more than one provider, for example a team of technicians or nurses, to a single patient, or multiple patients to one provider, for instance in a counseling or other group setting. For further example, while in embodiments the clinical data store 104 and provider data store 108 have generally been described as single databases, in further embodiments either of those data stores or others may be implemented as distributed or multiple systems. Other hardware, software or other resources described as singular may in embodiments be distributed, and similarly in embodiments resources described as distributed may be combined. The scope of the invention is accordingly intended to be limited only by the following claims.

We claim:

1. A system for automatically assigning clinical care providers to patients, comprising:
 a computerized clinical data store configured to store factors for a patient, the factors comprising one or more of patient acuity status, a patient workload estimate, patient morbidity status, patient mobility status, patient demographic data, patient immune condition status, patient infectious condition status, patient surgical status, patient ventilator status, patient life support status, patient pharmaceutical use status, patient one-to-one provider requirement status and patient preference data;
 a care provider data store configured to store care provider factors; the care provider factors comprising one or more of provider clinical qualifications, provider schedule, provider workload status and provider infectious exposure status;
 a first assignment engine on a first computer, the first assignment engine configured to communicate with the clinical data store and the care provider data store to automatically generate a first care provider assignment of the patient to a first clinical care provider based on comparison of at least one of the patient factors or provider factors, wherein the first care provider assignment is automatically generated by invoking a rules-based assignment engine to access a rule set comprising an ordered weighting of an analysis of patient acuity status compared to provider clinical qualifications, an analysis of continuity of patient care, an analysis of provider workload status incorporating a patient workload estimate, and provider preference data, wherein continuity of patient care identifies a care provider that has been previously assigned to the patient; and a reassignment engine, the reassignment engine communicating with the clinical data store and the care provider data store to automatically generate a reassignment of the patient to a second care provider by replacing the first care provider assignment based on a change that is received to one or more of the patient or care provider factors.

2. A system according to claim 1, wherein the patient factors comprise at least one of a patient chart, an electronic medical record, and a patient history.

3. A system according to claim 1, wherein the provider clinical qualifications comprise at least one of clinical certifications, experience level, and qualification for procedures or equipment operation.

4. A system according to claim 1, wherein the provider infectious exposure status comprises at least one of provider exposure to other potentially infectious patients, provider exposure to other potentially infectious providers, and provider exposure to potentially infectious sites.

5. A system according to claim 1, wherein the assignment engine comprises a rules-based assignment engine.

6. A system according to claim 5, wherein the rules-based assignment engine accesses a rule set to compare the patient factors to the provider factors.

7. A system according to claim 5, wherein the rule set is extensible.

8. A system according to claim 1, further comprising a management interface, communicating with the assignment engine, the management interface presenting an operator with a view of the results of the automatically generated patient assignments.

9. A system according to claim 8, wherein the management interface comprises a selector tool to permit the operator to accept or adjust the automatically generated patient assignments.

10. A system according to claim 9, wherein the management interface generates a contraindication notice to the operator when provider factors conflict with the patient factors for a provider assignment.

11. A system according to claim 1, wherein the provider is at least one of a nurse, a physician, a technician and a therapist.

12. A system according to claim 1, wherein the automatically generated patient assignments comprise assignments for at least one of a shift, a partial shift, a day, a week, a month, a case and an event.

13. A system according to claim 1, wherein generation of the automatically generated patient assignments is triggered by changed conditions comprising at least one of a change in patient census, a change in patient acuity, and a change in provider staffing or schedule.

14. A system according to claim 1, wherein the automatically generated patient assignments are based on prior automatically generated provider assignments generated to produce a minimum amount of assignment changes.

15. Computer storage media having computer-executable instructions stored thereon that, when executed by a computing device having a processor and memory, cause the computing device to perform a method for automatically assigning clinical care providers to patients, comprising:
   accessing patient factors associated with a clinical patient;
   accessing provider factors associated with a care provider;
   comparing the patient factors and the provider factors;
   invoking a rules-based assignment engine to automatically generate patient assignments by invoking a rules-based assignment engine to access a rule set comprising an ordered weighting of an analysis of patient acuity status compared to provider clinical qualifications, an analysis of continuity of patient care, an analysis of provider workload status incorporating a patient workload estimate, and provider preference data, wherein continuity of patient care identifies a care provider that has been previously assigned to the patient; and:
   automatically generating a patient reassignment by an assignment engine based on a change that is received to one or more of the patient factors and the provider factors.

16. The computer-readable media of claim 15, wherein the patient factors comprise at least one of a patient chart, an electronic medical record, and a patient history.

17. The computer-readable media of claim 16, wherein the patient factors comprise at least one of patient acuity status, a patient workload estimate, patient morbidity status, patient mobility status, patient demographic data, patient immune condition status, patient infectious condition status, patient surgical status, patient ventilator status, patient life support status, patient pharmaceutical use status, patient one-to-one provider requirement status and patient preference data.

18. The computer-readable media of claim 15, wherein the provider factors comprise at least one of provider clinical qualifications, provider schedule, provider workload status and provider infectious exposure status.

19. The computer-readable media of claim 18, wherein the provider clinical qualifications comprise at least one of clinical certifications, experience level, and qualification for procedures or equipment operation.

20. The computer-readable media of claim 18, wherein the provider infectious exposure status comprises at least one of provider exposure to other potentially infectious patients, provider exposure to other potentially infectious providers, and provider exposure to potentially infectious sites.

21. The computer-readable media of claim 15, wherein the rule set is extensible.

22. The computer-readable media of claim 15, further comprising presenting a management interface to an operator with a view of the results of the automatically generated patient assignments.

23. The computer-readable media of claim 22, wherein the management interface comprises a selector tool to permit the operator to accept or adjust the automatically generated patient assignments.

24. The computer-readable media of claim 23, further comprising generating a contraindication notice to the operator via the management interface when provider factors conflict with the patient factors for a provider assignment.

25. The computer-readable media of claim 15, wherein the provider is at least one of a nurse, a physician, a technician and a therapist.

26. The computer-readable media of claim 15, wherein the automatically generated patient assignments comprise assignments for at least one of a shift, a partial shift, a day, a week, a month, a case and an event.

27. The computer-readable media of claim 15, wherein the automatically generating is triggered by changed conditions comprising at least one of a change in patient census, a change in patient acuity, and a change in provider staffing or schedule.

28. The computer-readable media of claim 15, wherein the automatically generating comprises automatically generating patient assignments based on prior automatically generated provider assignments to produce a minimum amount of assignment changes.

29. A method for automatically generating an assignment of a clinical care provider to a patient, the assignment being generated according to a method comprising:
    utilizing a first computing process executed by a computing device, accessing patient factors associated with a clinical patient;
    utilizing a second computing process, accessing provider factors associated with a care provider;
    utilizing a third computing process, comparing the patient factors and the provider factors;
    utilizing a fourth computing process, invoking a rules-based assignment engine to access a rule set comprising an ordered weighting of an analysis of patient acuity status compared to provider clinical qualifications, an analysis of continuity of patient care, an analysis of provider workload status incorporating a patient workload estimate, and provider preference data, wherein continuity of patient care identifies a care provider that has been previously assigned to the patient;
    utilizing a fifth computing process, applying the rule set to the patient factors and the provider factors to automatically generate a patient assignment;
    utilizing a sixth computing process, automatically generating a patient assignment based on the outcome of applying the rule set; and
    utilizing a seventh computing process, presenting a management interface to an operator with a view of the results of the automatically generated patient assignment, wherein the first, second, third, fourth, fifth, sixth and seventh computing processes are performed by one or more computing devices.

30. The method according to claim 29, wherein the patient factors comprise at least one of a patient chart, an electronic medical record, and a patient history.

31. The method according to claim 30, wherein the patient factors comprise at least one of patient acuity status, a patient workload estimate, patient morbidity status, patient mobility status, patient demographic data, patient immune condition status, patient infectious condition status, patient surgical status, patient ventilator status, patient life support status, patient pharmaceutical use status, patient one-to-one provider requirement status and patient preference data.

32. The method according to claim 29, wherein the provider factors comprise at least one of provider clinical qualifications, provider schedule, provider workload status and provider infectious exposure status.

33. The method according to claim 32, wherein the provider clinical qualifications comprise at least one of clinical certifications, experience level, and qualification for procedures or equipment operation.

34. The method according to claim 32, wherein the provider infectious exposure status comprises at least one of provider exposure to other potentially infectious patients, provider exposure to other potentially infectious providers, and provider exposure to potentially infectious sites.

35. The method according to claim 29, wherein the automatically generating comprises:
    determining whether a threshold criteria is satisfied in the rule set; and
    generating a set of qualified providers for narrowing based on further factors.

36. The method according to claim 35, wherein the further factors include one or more of schedule preferences, staff seniority, and first-available status.

37. The method according to claim 29, wherein the rule set is extensible.

38. The method according to claim 29, wherein the management interface comprises a selector tool to permit the operator to accept or adjust the automatically-generated patient assignments.

39. The method according to claim 38, further comprising generating a contraindication notice to the operator via the management interface when provider factors conflict with the patient factors for a provider assignment.

40. The method according to claim 29, wherein the provider is at least one of a nurse, a physician, a technician and a therapist.

41. The method according to claim 29, wherein the automatically generated assignment comprises assignments for at least one of a shift, a partial shift, a day, a week, a month, a case and an event.

42. The method according to claim 29, wherein the automatically generating is triggered by changed conditions comprising at least one of a change in patient census, patient intake, patient discharge, patient status, patient acuity, provider staffing, available care provider personnel, clinical staffing, or schedule.

43. The method according to claim 29, wherein the automatically generating comprises automatically generating a patient assignment based on a prior automatically generated provider assignment to produce a minimum amount of assignment change.

44. Non-transitory computer-readable media having computer executable instructions embodied thereon that, when executed by a computing device having a processor and a memory, cause the computing device to perform a method for excluding care providers from assignment to patients based on infectious status, comprising:
    accessing an immune condition status associated with a patient;
    accessing an infectious exposure status associated with a provider; and
    automatically excluding the care provider from assignment to the patient by:
        (1) invoking a rules-based assignment engine comparing the infectious exposure status of the provider with the immune condition status of the patient, wherein the rules-based assignment engine accesses a rule set including at least an ordered weighting of an analysis of patient acuity status compared to provider clinical qualifications, an analysis of patient care, an analysis of provider workload status incorporating a patient workload estimate, and provider preference data, wherein continuity of patient care identifies a care provider that has been previously assigned to the patient,
        (2) the assignment engine creating an electronic exclusion of the care provider based on a conflict between the infectious exposure status and the immune condition status; and
        (3) displaying a notice of the electronic exclusion on a management interface presented to an operator.

45. The computer-readable media of claim 44, wherein the infectious exposure status is determined at least in part by examination of one or more of patient assignment history, exposure to other potentially infectious patients, exposure to other potentially infectious providers, and exposure to potentially infectious sites.

46. The computer-readable media of claim 44, wherein the provider is at least one of a nurse, a physician, a technician and a therapist.

47. The computer-readable media of claim 44, wherein the infectious exposure status is tracked for a clinically relevant window of time after a prior potential infectious exposure.

* * * * *